(12) United States Patent
Kitagawa et al.

(10) Patent No.: US 11,613,089 B2
(45) Date of Patent: Mar. 28, 2023

(54) METHOD FOR PRODUCING MEDICAL DEVICE

(71) Applicant: TORAY INDUSTRIES, INC., Tokyo (JP)

(72) Inventors: Rumiko Kitagawa, Otsu (JP); Masataka Nakamura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 17/788,546

(22) PCT Filed: Jan. 6, 2021

(86) PCT No.: PCT/JP2021/000185
§ 371 (c)(1),
(2) Date: Jun. 23, 2022

(87) PCT Pub. No.: WO2021/145249
PCT Pub. Date: Jul. 22, 2021

(65) Prior Publication Data
US 2023/0057266 A1    Feb. 23, 2023

(30) Foreign Application Priority Data
Jan. 16, 2020   (JP) .............................. JP2020-004872

(51) Int. Cl.
*B29D 11/00*     (2006.01)
(52) U.S. Cl.
CPC .............................. *B29D 11/00038* (2013.01)
(58) Field of Classification Search
CPC ............................................. B29D 11/00038
See application file for complete search history.

(56) References Cited

U.S. PATENT DOCUMENTS

| | | | |
|---|---|---|---|
| 6,039,872 A * | 3/2000 | Wu ...................... | B01D 69/141 210/500.35 |
| 2019/0015542 A1 | 1/2019 | Kitagawa et al. | |
| 2019/0022282 A1 | 1/2019 | Kitagawa et al. | |
| 2020/0139653 A1 | 5/2020 | Kitagawa et al. | |
| 2020/0215226 A1 | 7/2020 | Kitagawa et al. | |

FOREIGN PATENT DOCUMENTS

| | | |
|---|---|---|
| JP | 2013-119555 A | 6/2013 |
| WO | WO 2017/146101 A1 | 8/2017 |
| WO | WO 2017/146102 A1 | 8/2017 |
| WO | WO 2018/207644 A1 | 11/2018 |
| WO | WO 2019/031477 A1 | 2/2019 |

OTHER PUBLICATIONS

International Search Report, issued in PCT/JP2021/000185, PCT/ISA/210, dated Mar. 16, 2021.
Written Opinion of the International Searching Authority, issued in PCT/JP2021/000185, PCT/ISA/237, dated Mar. 16, 2021.

* cited by examiner

*Primary Examiner* — James C. Jones
(74) *Attorney, Agent, or Firm* — Birch, Stewart, Kolasch & Birch, LLP

(57) ABSTRACT

A method of producing a medical device having a substrate and a hydrophilic polymer layer, including the steps of: pretreating the substrate by placing the substrate in an alkali solution and heating the substrate at a temperature ranging from 50° C. to 100° C.; and heating a solution containing the pretreated substrate, a hydrophilic polymer having an acidic group and a hydroxyalkyl group, and an organic acid at a temperature ranging from 50° C. to 100° C. Provided is a simple method of producing a medical device imparted with hydrophilicity excellent in durability.

12 Claims, No Drawings

METHOD FOR PRODUCING MEDICAL DEVICE

TECHNICAL FIELD

The present invention relates to methods of producing medical devices.

BACKGROUND ART

There have hitherto been used devices using soft materials made of resins such as a silicone rubber and hydrogel and devices using hard materials such as metal and glass in various applications in various fields.

Applications of devices using soft materials include medical devices for introduction into a living body and for covering a surface of a living body, biotechnology devices such as cell culture sheets and scaffold materials for tissue regeneration, and cosmetic devices such as facial packs.

Applications of devices using hard materials include electric appliances such as personal computers, mobile phones, displays, etc., ampules for use in injections, and use as diagnostic and analysis tools such as capillaries, biosensing chips, and the like.

In use of various devices, such as medical devices that are introduced into a living body or affixed to the surface of a living body, if it is possible to impart better properties such as hydrophilicity, lubricity, biocompatibility, and medicinal effects than before surface modification to the medical device by surface modification, an improvement in tactile sensation, reduction of discomfort, improvements of symptoms, and the like in users (patients, etc.) can be expected.

Various methods using alkali treatment have been known as methods for modification of the surface of a substrate in medical devices.

For example, Patent Literature 1 discloses a method of imparting good water wettability to the surface of a substrate by heating the substrate in a solution containing a polymer having a hydroxy group with pH from 2.0 to 6.0. Patent Literature 1 also discloses that pretreatment with acid or alkali may further be performed.

For example, Patent Literature 2 discloses a hydrophilic membrane with the surface having anionic hydrophilic groups treated (applied) with an alkali compound solution to improve the anti-fog properties of the surface.

CITATION LIST

Patent Literature

Patent Literature 1: WO 2019/031477
Patent Literature 2: JP 2013-119555 A

SUMMARY OF INVENTION

Technical Problem

However, the present inventors intensively studied to find that the modification effect on the substrate surface at lower than 100° C. by the method described in Patent Literature 1 was not necessarily sufficient.

Such a method as described in Patent Literature 2, comprising preparing a substrate surface having an anionic hydrophilic group, and then treating the substrate surface with an alkaline compound to form a hydrophilic membrane, requires the steps, for preparing a surface having an anionic hydrophilic group, of applying a coating solution comprising 4 or more raw materials to a substrate, drying it using a hot-air dryer, allowing it to pass near an electrodeless discharge lamp, washing it with running water, and drying it, and may lead to increase in the production cost due to the large number of steps. In addition, the substrate to be used is limited to substrates having an anionic group on the surface. Furthermore, the method improves the hydrophilicity but does not improve the lubricity, and thus the substrate is not preferred for use as a medical material used on the surface of living body that requires lubricity.

The present invention has been made in view of the aforementioned problems of conventional art. Thus, the present invention aims to provide a production method in which a hydrophilic polymer layer excellent in durability is imparted to a substrate surface using less types of materials in a simple manner without need of pressurization.

Solution to Problem

To achieve the above object, the present invention provides the following;

A method of producing a medical device comprising a substrate and a hydrophilic polymer layer, comprising the steps of:

placing the substrate in an alkali solution and heating the substrate at a temperature ranging from 50° C. to 100° C. to obtain a pretreated substrate; and placing the pretreated substrate in a solution containing a hydrophilic polymer having an acidic group and a hydroxyalkyl group, and an organic acid, and heating the pretreated substrate at a temperature ranging from 50° C. to 100° C.

Advantageous Effects of Invention

According to the present invention, a hydrophilic polymer layer excellent in durability can be imparted to a medical device surface using less types of materials in a simple manner without need of pressurization.

DESCRIPTION OF EMBODIMENTS

The present invention relates to a method of producing a medical device comprising a substrate and a hydrophilic polymer layer.

In the present invention, the shape of the medical device is, for example, a lenticular, tubular, sheet, film, or container-like shape.

Examples of a lenticular medical device include an ophthalmic lens, such as a contact lens, an intraocular lens, an artificial cornea, a corneal inlay, a corneal onlay, and an eyeglass lens. An ophthalmic lens, especially a contact lens is one of the most preferred embodiments of the present invention.

Examples of a tubular medical device include an infusion tube, a gas delivery tube, a drainage tube, a blood circuit, a coating tube, a catheter, a stent, a sheath, a tube connector, an access port, and a hollow fiber for heart-lung machine.

Examples of a sheet or film medical device include a skin dressing material, a wound dressing material, a skin protection material, a skin medicine carrier, a biosensor chip, and an endoscope covering material.

Examples of a medical device having a container-like shape include a drug carrier, a cuff, and a drainage bag.

In the present invention, the medical device preferably is an ophthalmic lens, a skin dressing material, a wound dressing material, a skin protection material, a skin medicine carrier, an infusion tube, a gas delivery tube, a drainage tube, a blood circuit, a coating tube, a catheter, a stent, a sheath, a biosensor chip, or a covering material for heart-lung machine or an endoscope. More preferably, the medical device is an ophthalmic lens. As described above, in one of the most preferred embodiments of the present invention, the ophthalmic lens is a contact lens. The contact lens may be a contact lens for an orthoptic or cosmetic purpose.

In the present invention, it is possible to use, as a substrate of the medical device, both a hydrous substrate and a non-hydrous substrate. Examples of the material of the hydrous substrate include a hydrogel and a silicone hydrogel. The silicone hydrogel is particularly preferable because of having flexibility which imparts excellent comfort, and high oxygen permeability. Examples of the non-hydrous substrate include a low water content soft material and a low water content hard material. That is, in the method of producing a medical device of the present invention, the substrate preferably comprises one or more material selected from the group consisting of a hydrogel, a silicone hydrogel, a low water content soft material, and a low water content hard material.

The present invention is applicable to both an ordinary hydrogel containing no silicone and a hydrogel containing silicone (hereinafter referred to as "silicone hydrogel") in the case of materials for the hydrous substrate. It is possible to use particularly suitably for the silicone hydrogel since surface physical properties can be significantly improved.

Hereinafter, the United States Adopted Names (USAN) may be used to refer to materials. In the USAN, there are cases where variations of a material are expressed by adding symbols such as A. B, and C at the end. However, as used herein, all variations are expressed when no symbol is added at the end. For example, when simply written as "ocufilcon", it expresses all variations, such as "ocufilcon A", "ocufilcon B", "ocufilcon C", "ocufilcon D", "ocufilcon E", and "ocufilcon F."

In the method of producing a medical device of the present invention, the hydrogel is preferably a hydrogel selected from the group consisting of tefilcon, tetrafilcon, helfilcon, mafilcon, polymacon, hioxifilcon, alfafilcon, omafilcon, hioxifilcon, nelfilcon, nesofilcon, hilafilcon, acofilcon, deltafilcon, etafilcon, focofilcon, ocufilcon, phemfilcon, methafilcon, and vilfilcon.

For example, in the case of hydrogel contact lens, it is classified into contact lens classification Groups 1 to 4 defined by Food and Drug Administration (FDA). Especially, Group 2 and Group 4 are more preferable, and Group 4 is particularly preferable because of exhibiting good water wettability and antifouling properties.

Group 1 represents a nonionic hydrogel lens having a moisture content of less than 50% by mass. Specific examples thereof include tefilcon, tetrafilcon, helfilcon, mafilcon, polymacon, and hioxifilcon.

Group 2 represents a nonionic hydrogel lens having a moisture content of 50% by mass or more. Specific examples thereof include alfafilcon, omafilcon, hioxifilcon, nelfilcon, nesofilcon, hilafilcon, and acofilcon. Omafilcon, hioxifilcon, nelfilcon, and nesofilcon are more preferable, omafilcon and hioxifilcon are still more preferable, and omafilcon is particularly preferable because of exhibiting satisfactory water wettability and antifouling properties.

Group 3 represents an ionic hydrogel lens having a moisture content of less than 50% by mass. A specific example thereof includes deltafilcon.

Group 4 represents an ionic hydrogel lens having a moisture content of 50% by mass or more. Specific examples thereof include etafilcon, focofilcon, ocufilcon, phemfilcon, methafilcon, and vilfilcon. Etafilcon, focofilcon, ocufilcon, and phemfilcon are more preferable, etafilcon and ocufilcon are still more preferable, and etafilcon is particularly preferable because of exhibiting satisfactory water wettability and antifouling properties.

Specific example of the silicone hydrogel in the case of, for example, a silicone hydrogel contact lens, is preferably a silicone hydrogel selected from the group belonging to contact lens classification Group 5 defined by Food and Drug Administration (FDA).

The silicone hydrogel is preferably a polymer which has a silicon atom in the main chain and/or side chain and has hydrophilicity, and examples thereof include a copolymer of a monomer having a siloxane bond and a hydrophilic monomer.

Specifically, the silicone hydrogel is preferably a silicone hydrogel selected from the group consisting of lotrafilcon, galyfilcon, narafilcon, senofilcon, comfilcon, enfilcon, balafilcon, efrofilcon, fanfilcon, somofilcon, samfilcon, olifilcon, asmofilcon, formofilcon, stenfilcon, abafilcon, mangofilcon, riofilcon, sifilcon, larafilcon, and delefilcon. Especially, lotrafilcon, galyfilcon, narafilcon, senofilcon, comfilcon, enfilcon, stenfilcon, somofilcon, delefilcon, balafilcon, and samfilcon are more preferable, lotrafilcon, narafilcon, senofilcon, comfilcon, and enfilcon are still more preferable, and narafilcon, senofilcon, and comfilcon are particularly preferable because of exhibiting satisfactory water wettability and lubricity.

The low water content soft material and the low water content hard material are preferably a material having a silicon atom because of exhibiting high oxygen permeability capable of supplying sufficient oxygen to the cornea in the case of, for example, use in a medical device such as an ophthalmic lens.

For example, when the low water content hard material is a contact lens, specific example of the low water content hard material is preferably a low water content hard material selected from the group belonging to contact lens classification defined by Food and Drug Administration (FDA).

Such a low water content hard material is preferably a polymer having a silicon atom in the main chain and/or side chain. Examples thereof include polymers having a siloxane bond. Among these polymers having a silicon atom, those in which the silicon atom is contained in the polymer by a siloxane bond are preferable from the viewpoint of the oxygen permeability. Specific examples of such polymers include tris(trimethylsilyloxy)silylpropyl methacrylate, polydimethylsiloxane having a double bond at both the ends, homopolymers using silicone-containing (meth)acrylate, and copolymers of these monomers and other monomers.

Specifically, the low water content hard material is preferably a material selected from the group consisting of neofocon, pasifocon, telefocon, silafocon, paflufocon, petrafocon, and fluorofocon. Especially, neofocon, pasifocon, telefocon, and silafocon are more preferable, neofocon, pasifocon, and telefocon are still more preferable, and neofocon is particularly preferable because of exhibiting satisfactory water wettability and antifouling properties.

In the present invention, when the medical device is other than a contact lens, suitable examples of the low water content hard material include polyethylene, polypropylene, polysulfone, polyetherimide, polystyrene, polymethyl methacrylate, polyamide, polyester, an epoxy resin, polyurethane, and polyvinyl chloride. Especially, the low water content hard material is more preferably polysulfone, polystyrene, polymethyl methacrylate, or polyamide, and is particularly preferably polymethyl methacrylate because of exhibiting satisfactory water wettability and antifouling properties.

Specific examples of the low water content soft material include low water content soft materials used in medical devices as mentioned in WO2013/024799, in which the moisture content is 10% by mass or less, the elastic modulus is 100 kPa or more and 2,000 kPa or less, and the tensile elongation is 50% or more and 3,000% or less. Elastofilcon is also suitable.

In the present invention, when the medical device is other than ophthalmic lenses, suitable examples of the low water content soft material include silicone elastomers, soft polyurethane, polyvinyl acetate, ethylene-vinyl acetate copolymers, soft polyester resins, soft acrylic resins, soft polyvinyl chloride, natural rubber, and various synthetic rubbers.

According to the present invention, it is possible to impart moderate hydrophilicity (water wettability) to the surface of the medical device whether the substrate is hydrous or low hydrous. Therefore, the moisture content of the substrate may be from 0 to 99% by mass. The moisture content of the substrate is preferably 0.0001% by mass or more, and particularly preferably 0.001% by mass or more, since the effect of imparting moderate hydrophilicity to the surface of the medical device is further enhanced. The moisture content of the substrate is preferably 60% by mass or less, more preferably 50% by mass or less, and still more preferably 40% by mass or less.

When the medical device is a contact lens, since it is easy to ensure the movement of the lens in eyes, the moisture content of the substrate is preferably 15% by mass or more, and sill more preferably 20% by mass or more.

The method of producing a medical device in the present invention comprises placing a pretreated substrate as described later in a solution containing a hydrophilic polymer having an acidic group and a hydroxyalkyl group, and an organic acid, and heating the substrate at a temperature ranging from 50° C. to 100° C.

In the present invention, pretreatment is a step performed before the step of placing a substrate in a solution containing a hydrophilic polymer and an organic acid and heating it, and refers to a step of placing the substrate in an alkali solution and heating the substrate at a temperature ranging from 50° C. to 100° C.

Here, alkali means a compound exhibiting basicity in water. Examples of alkalis include organic alkaline compounds representatively including tertiary amines and phosphines; inorganic alkaline compounds representatively including potassium hydroxide, sodium hydroxide, calcium hydroxide, calcium carbonate, potassium hydrogencarbonate, sodium carbonate, sodium hydrogencarbonate, lithium hydrogencarbonate, and sodium dithionite (sodium hydrosulfite); and organic metal salt-based alkaline compounds such as sodium methoxide and potassium t-butoxide. Among them, inorganic alkaline compounds are preferable in terms of low costs and relatively high safety of the compounds. Specifically, a compound selected from potassium hydroxide, sodium hydroxide, calcium hydroxide, calcium carbonate, potassium hydrogencarbonate, and sodium hydrogencarbonate is more preferable; a compound selected from potassium hydroxide, sodium hydroxide, calcium hydroxide, and calcium carbonate is still more preferable; and sodium hydroxide is most preferable.

The solvent in the alkali solution is preferably a highly polar solvent in terms of solubility. Examples include alcohols such as methanol, ethanol, isopropyl alcohol, n-propanol, n-butanol, ethylene glycol monomethyl ether, and 1,2-propylene glycol monomethyl ether; nitrogen-containing solvents such as acetonitrile and N,N-dimethyl formamide; sulfur-containing solvents such as dimethyl sulfoxide: water; and mixed solvents thereof. Among them, a solvent selected from alcohols, water, and mixed solvents thereof is preferable, and a solvent selected from ethanol, water, and mixed solvents thereof is more preferable, because of relatively high solubility.

The concentration of an alkali dissolved in a solvent varies depending on the selected solvent, and may be preferably from 0.001 mob/L to 30 mol/L. Too high concentration of the alkali significantly affects the strength of the medical device itself, while too low concentration results in difficulty of obtaining a surface with durable and good water wettability. The concentration of the alkali is more preferably from 0.01 to 20 mol/L, still more preferably from 0.02 to 10 mol/L, and particularly preferably from 0.03 to 5 mol/L.

In the pretreatment, too high pH of the alkali solution significantly affects the strength of the medical device itself, while too low pH results in difficulty of obtaining a surface with durable and good water wettability, and thus the range of the pH of the alkali solution is preferably within a range from 8.0 to 14.0. The pH of the alkali solution is preferably 9.0 or higher, more preferably 9.4 or higher, still more preferably 9.6 or higher, and particularly preferably 9.8 or higher. The pH is more preferably 13.9 or lower, still more preferably 13.7 or lower, yet more preferably 13.5 or lower, and yet still preferably 13.3 or lower.

The pH of the solution can be measured using a pH meter (e.g., pH meter Eutech pH 2700 (Eutech Instruments)). Here, the pH of the alkali solution means the pH value measured after adding the alkali to the solution, followed by stirring at room temperature (20 to 25° C.) for 30 minutes with a rotor to make the solution uniform, and before placing a substrate in the solution and heating the substrate. In the present invention, the pH value is rounded off to one decimal place.

The present inventors have found that a very simple method comprising placing a substrate that has been pretreated with an alkali solution as described above in a solution containing a hydrophilic polymer having an acidic group and a hydroxyalkyl group, and an organic acid, and heating the substrate at a temperature ranging from 50° C. to 100° C. enables imparting excellent water wettability, lubricity, and the like to the medical device. These processes can be performed at a low temperature of 100° C. or lower, and thus do not require pressurization.

Examples of methods for heating in pretreatment in the alkali solution include a heating method (hot air), a high-pressure steam sterilization method, irradiation with electromagnetic waves (γ ray, infrared light, microwave, etc.), a dry heat method, and a flame method. From the viewpoint of the water wettability, lubricity, and shortening of the production process, a heating method (hot air) is most preferable. A constant-temperature oven or a hot air circulating oven is preferably used as the apparatus.

The temperature at which the solution is heated in pretreatment of the substrate in the alkali solution is within a range from 50° C. to 100° C. from the viewpoints of obtaining a medical device surface exhibiting good water wettability and lubricity, and exerting less influence on the strength of the medical device itself. The heating temperature is more preferably 51° C. or lower, still more preferably 55° C. or lower, and particularly preferably 60° C. or lower.

The heating temperature is more preferably 99° C. or lower, still more preferably 95° C. or lower, and particularly preferably 90° C. or lower.

According to the study by the present inventors, when a substrate is heated at a temperature ranging from 50° C. to 100° C. in pretreatment using an alkali solution, and when the step of heating the pretreated substrate in a solution of a hydrophilic polymer having an acidic group and a hydroxyalkyl group is under the temperature condition of from 50° C. to 100° C., then the hydrophilic polymer can be strongly immobilized on the surface of the substrate. Here, pressurization is not performed during the heating step.

As a conventional art, there is a known method in which a hydrophilic polymer having a hydroxy group is immobilized on the surface of a substrate under a pressurized condition in an autoclave (see, for example, WO2017/146102). When a substrate is not heated in pretreatment using an alkali solution, and w % ben the step of heating the pretreated substrate in a hydrophilic polymer solution is under the temperature condition of 100° C. or lower, i.e., when under a non-pressurized condition, then the hydrophilic polymer is weakly immobilized on the surface of the substrate. That is, sufficient durability is not obtained.

That is, an alkali treatment that is pretreatment of a substrate, performed under a heating condition within a range from 50° C. to 100° C., and subsequent immobilization of a hydrophilic polymer having an acidic group and a hydroxyalkyl group to the substrate enable immobilization under a low-temperature condition without need of pressurization.

The mechanism for this is unknown, but it is estimated that alkali treatment as pretreatment of a substrate, performed within a range from 50° C. to 100° C., results in hydrolysis of the substrate component and appropriate formation of hydroxyl or other groups on the surface, which groups then form intermolecular forces, such as hydrogen bond, with the hydrophilic polymer having an acidic group and a hydroxyalkyl group during subsequent steps, whereby the hydrophilic polymer layer can be immobilized on the surface of the substrate even under a low-temperature condition without need of pressurization.

The heating time period in pretreatment of a substrate in an alkali solution is preferably from 5 minutes to 600 minutes, because too short time period leads to a difficulty in obtaining a medical device surface exhibiting good water wettability and lubricity, and too long time period may affect the strength of the medical device itself. The heating time is more preferably 10 minutes or more, and still more preferably 15 minutes or more. The heating time is more preferably 400 minutes or less, and still more preferably 300 minutes or less.

The hydrophilic polymer used in the method of producing a medical device in the present invention is, usually, a different material from the substrate. However, the substrate and the hydrophilic polymer may be made of the same material, or the same material as the hydrophilic polymer may be used as a part of the substrate, as long as the substrate can maintain predetermined effects.

The hydrophilic polymer used in the present invention is soluble in 100 parts by mass of water or a mixture of 100 parts by mass of water and 100 parts by mass of tert-butanol at room temperature (20 to 25° C.) in the amount of preferably 0.0001 parts by mass or more, more preferably 0.01 parts by mass or more, still more preferably 0.1 parts by mass or more, and particularly preferably 1 part by mass or more.

The hydrophilic polymer used in the present invention preferably has a molecular weight of 2,000 to 1,500,000. The molecular weight is more preferably 5,000 or more, and still more preferably 10,000 or more. The molecular weight is more preferably 1,200,000 or less, and still more preferably 1,000,000 or less. Here, a weight average molecular weight in terms of polyethylene glycol or polyethylene oxide measured by a gel permeation chromatography method (aqueous solvent) is used as the molecular weight.

With respect to the concentration of a hydrophilic polymer in the solution during production, too high concentration may lead to an increase in difficulty of handling during manufacture due to an increase in viscosity. Thus, in the method of producing a medical device in the present invention, the concentration of a hydrophilic polymer in the hydrophilic polymer solution ranges preferably from 0.01 to 20% by mass. The concentration of the hydrophilic polymer is more preferably 0.02% by mass or more, and still more preferably 0.03% by mass or more. The concentration of the hydrophilic polymer is more preferably 15% by mass or less, still more preferably 10% by mass or less, yet more preferably 5% by mass, and most preferably 1% by mass or less.

In the method of producing a medical device in the present invention, the hydrophilic polymer has an acidic group and a hydroxyalkyl group. The hydrophilic polymer having an acidic group and a hydroxyalkyl group is preferable because it enables formation of a surface with durable water-wettability and because it enables formation of a surface having excellent antifouling properties against body fluids and the like. Specifically, the acidic group is preferably a group selected from a carboxy group and a sulfonic group, and particularly preferably a carboxy group. The carboxy group or the sulfonic group may be in the form of a salt.

Specifically, the hydroxyalkyl group is preferably a group selected from hydroxyalkyl groups having 1 to 20 carbon atoms, such as a hydroxymethyl group, a hydroxyethyl group, a hydroxypropyl group, a hydroxyisopropyl group, a hydroxybutyl group, a hydroxy-t-butyl group, a hydroxydecyl group, a hydroxydodecyl group, or a hydroxyoctadecyl group, more preferably a hydroxyalkyl group having 2 to 8 carbon atoms, and particularly preferably a hydroxyethyl group.

The polymer having an acidic group and a hydroxyalkyl group may be, for example, a copolymer of a monomer having an acidic group and a monomer having a hydroxyalkyl group. The hydrophilic monomer constituting the copolymer is preferably a monomer having a group selected from an allyl group, a vinyl group, and a (meth)acryloyl group because of its high polymerizability, and particularly preferably a monomer having a (meth)acryloyl group. One or more of the monomers may be copolymerized.

Examples of suitable monomers having an acidic group as such monomers include (meth)acrylic acid, vinylbenzoic acid, thiophene-3-acetic acid, 4-styrenesulfonic acid, vinylsulfonic acid, 2-acrylamido-2-methylpropanesulfonic acid, and salts thereof. Of these, a monomer selected from (meth)acrylic acid, 2-acrylamido-2-methylpropanesulfonic acid, and salts thereof is more preferable, and a monomer selected from (meth)acrylic acid, and salts thereof is particularly preferable.

Examples of the monomer having a hydroxyalkyl group include hydroxyethyl(meth)acrylate, hydroxypropyl(meth)acrylate, hydroxybutyl(meth)acrylate, hydroxyethyl(meth)acrylamide, and caprolactone-modified 2-hydroxyethyl(meth)acrylate. Of these, a monomer selected from hydroxyethyl(meth)acrylate, hydroxypropyl(meth)acrylate, and hydroxyethyl(meth)acrylamide is preferable, and hydroxyethyl(meth)acrylate is particularly preferable, in view of improving ease of polymerization and antifouling properties against body fluids. One or more of the monomers may be copolymerized.

Preferred specific examples of the hydrophilic polymer having an acidic group and a hydroxyalkyl group include (meth)acrylic acid/hydroxyethyl(meth)acrylate copolymers, (meth)acrylic acid/hydroxypropyl(meth)acrylate copolymers, (meth)acrylic acid/hydroxybutyl(meth)acrylate copolymers, 2-acrylamido-2-methylpropanesulfonic acid/hydroxyethyl(meth)acrylate copolymers, 2-acrylamido-2-methylpropanesulfonic acid/hydroxypropyl(meth)acrylate copolymers, and 2-acrylamido-2-methylpropanesulfonic acid/hydroxybutyl(meth)acrylate copolymers. (Meth)acrylic acid/hydroxyethyl(meth)acrylate copolymers are particularly preferable.

When using a copolymer of a monomer having an acidic group and a monomer having a hydroxyalkyl group as a hydrophilic polymer, the copolymerization ratio thereof is preferably in a range of 1/99 to 99/1 in terms of [mass of the monomer having an acidic group]/[mass of the monomer having a hydroxyalkyl group]. The copolymerization ratio of the monomer having an acidic group is more preferably 2% by mass or more, still more preferably 5% by mass or more, and yet more preferably 10% by mass or more. The copolymerization ratio of the monomer having an acidic group is more preferably 80% by mass or less, still more preferably 70% by mass or less, and yet more preferably 60% by mass or less. The copolymerization ratio of the monomer having a hydroxyalkyl group is more preferably 10% by mass or more, still more preferably 20% by mass or more, and yet more preferably 30% by mass or more. The copolymerization ratio of the monomer having a hydroxyalkyl group is more preferably 80% by mass or less, still more preferably 70% by mass or less, and yet more preferably 60% by mass or less. When the copolymerization ratios of the monomer having an acidic group and the monomer having a hydroxyalkyl group are in the above range, functions such as durable water wettability and antifouling properties against body fluids are easily developed.

In the method of producing a medical device in the present invention, the hydrophilic polymer preferably has an amide group in addition to an acidic group and a hydroxyalkyl group, because a surface having not only water wettability but also lubricity can be formed.

When the hydrophilic polymer has an amide group in addition to an acidic group and a hydroxyalkyl group, the hydrophilic polymer exhibits moderate viscosity when dissolved in water, so that a surface having not only water wettability but also lubricity can be formed.

The hydrophilic polymer having an amide group in addition to an acidic group and a hydroxyalkyl group may be, for example, a copolymer of a monomer having an acidic group, a monomer having a hydroxyalkyl group, and a monomer having an amide group.

In view of ease of polymerization, the monomer having an amide group is preferably a monomer selected from a monomer having a (meth)acrylamide group and N-vinylcarboxylic acid amide (including cyclic one). Suitable examples of such a monomer include N-vinylpyrrolidone, N-vinylcaprolactam, N-vinylacetamide. N-methyl-N-vinylacetamide, N-vinylformamide, N,N-dimethylacrylamide, N,N-diethylacrylamide, N-isopropylacrylamide, N-(2-hydroxyethyl)acrylamide, acryloyl morpholine, and acrylamide. Of these, N-vinylpyrrolidone and N,N-dimethylacrylamide are preferable, and N,N-dimethylacrylamide is particularly preferable, in view of the lubricity.

Preferred specific examples of a copolymer of a hydrophilic polymer having an amide group in addition to an acidic group and a hydroxyalkyl group include (meth)acrylic acid/hydroxyethyl(meth)acrylate/N-vinylpyrrolidone copolymers, (meth)acrylic acid/hydroxyethyl(meth)acrylate/N,N-dimethyl acrylamide copolymers, (meth)acrylic acid/hydroxypropyl(meth)acrylate/N-vinylpyrrolidone copolymers, (meth)acrylic acid/hydroxypropyl(meth)acrylate/N,N-dimethylacrylamide copolymers, (meth)acrylic acid/hydroxybutyl(meth)acrylate/N-vinylpyrrolidone copolymers, (meth)acrylic acid/hydroxybutyl(meth)acrylate/N,N-dimethylacrylamide copolymers, 2-acrylamido-2-methylpropanesulfonic acid/hydroxyethyl(meth)acrylate/N-vinylpyrrolidone copolymers. 2-acrylamido-2-methylpropanesulfonic acid/hydroxyethyl(meth)acrylate/N,N-dimethyl acrylamide copolymers, 2-acrylamido-2-methylpropanesulfonic acid/hydroxypropyl(meth)acrylate/N-vinylpyrrolidone copolymers, 2-acrylamido-2-methylpropanesulfonic acid/hydroxypropyl(meth)acrylate/N,N-dimethyl acrylamide copolymers, 2-acrylamido-2-methylpropanesulfonic acid/hydroxybutyl(meth)acrylate/N-vinylpyrrolidone copolymers, and 2-acrylamido-2-methylpropanesulfonic acid/hydroxybutyl(meth)acrylate/N,N-dimethyl acrylamide copolymers. (Meth)acrylic acid/hydroxyethyl(meth)acrylate/N,N-dimethyl acrylamide copolymers are particularly preferable.

One or more monomers without acidic group or hydroxyalkyl group can also be copolymerized.

Suitable examples of the monomer without acidic group or hydroxyalkyl group include glycerol (meth)acrylate, N-(4-hydroxyphenyl)maleimide, hydroxystyrene, and vinyl alcohol (carboxylic acid vinyl ester as a precursor). In view of improving the antifouling properties against body fluids, glycerol (meth)acrylate and vinyl alcohol are preferable, and glycerol (meth)acrylate is particularly preferable.

It is also possible to use a monomer having functions such as hydrophilicity, antibacterial properties, antifouling properties, and medicinal effects.

Specific examples of the monomer having antibacterial properties include a monomer having a quaternary ammonium salt. Examples thereof include monomers having antibacterial properties, such as imidazolium salt monomer disclosed in JP 2010-88858 A, as well as (3-acrylamidepropyl)trimethylammonium chloride, trimethyl-2-methachloryloxyethylammonium chloride, and 2-methacryloyloxyethyl phosphorylcholine.

When a copolymer of a monomer having an acidic group and a monomer having a hydroxyalkyl group is copolymerized with one monomer having an amide group or a monomer having no acidic group or hydroxyalkyl group (hereinafter both referred to as "third monomer component"), the copolymerization ratio of the monomer having an acidic group is more preferably 5% by mass or more, still more preferably 10% by mass or more, and yet more preferably 25% by mass or more. The copolymerization ratio of the monomer having an acidic group is more preferably 90% by mass or less, still more preferably 80% by mass or less, and yet more preferably 70% by mass or less. The copolymerization ratio of the monomer having a hydroxyalkyl group is more preferably 5% by mass or more, still more preferably 10% by mass or more, and yet more preferably 25% by mass or more. The copolymerization ratio of the monomer having a hydroxyalkyl group is more preferably 90% by mass or less, still more preferably mass 80% or less, and yet more preferably 70% by mass or less. The copolymerization ratio of the third monomer component is more preferably 5% by mass or more, still more preferably 10% by mass or more, and yet more preferably 25% by mass or more. The copolymerization ratio of the third monomer component is more preferably 90% by mass or less, still more preferably 80% by mass or less, and yet more preferably 70% by mass or less.

When the copolymerization ratios of the monomer having an acidic group, the monomer having a hydroxyalkyl group, and the third monomer component are in the above range, functions such as lubricity and antifouling properties against body fluid are easily developed.

As long as properties required to the medical device are not impaired, additives other than the above materials may be included in the hydrophilic polymer layer. In addition to the hydrophilic polymer having an acidic group and a hydroxyalkyl group, one or more other hydrophilic polymers may be included in the hydrophilic polymer layer. Due to the tendency for the producing method to be more complex, it is preferable that the hydrophilic polymer layer is made of only one hydrophilic polymer having an acidic group and a hydroxyalkyl group.

Here, one polymer means a polymer or a polymer group (isomers, complexes, etc.) produced by one synthesis reaction. In the case of a copolymerized polymer using a plurality of monomers, even though the constituting monomer species are the same, polymers synthesized with the compounding ratio changed are not said to be the same one polymer.

The expression that the hydrophilic polymer layer is made of only one hydrophilic polymer having an acidic group and a hydroxyalkyl group means that, preferably, the hydrophilic polymer layer does not contain any polymer other than the hydrophilic polymer having an acidic group and a hydroxyalkyl group, or even when the layer contains other polymers, it means that the content of the other polymers is preferably 3 parts by mass or less based on 100 parts by mass of the hydrophilic polymer having an acidic group and a hydroxyalkyl group. The content of the other polymers is more preferably 0.1 parts by mass or less, and still more preferably 0.0001 parts by mass or less.

Even when the hydrophilic polymer layer contains a basic polymer as other polymer, transparency problems can be prevented as long as the amount of the basic polymer is within the range described above. In conventional art, a combination of an acidic polymer and a basic polymer is used to form a hydrophilic polymer layer on the surface of a substrate by electrostatic adsorption. According to the present invention, however, a hydrophilic polymer layer comprising only one polymer can be formed on the surface of a substrate.

When the hydrophilic polymer layer contains a basic polymer, the number ratio of the basic group/acidic group in the hydrophilic polymer layer is preferably 0.2 or less. The number ratio of the basic group/acidic group is more preferably 0.1 or less, and still more preferably 0.05 or less because of no formation of a salt derived from the reaction between the acidic group and the basic group, and excellent transparency. The basic group represents a basic functional group, and examples thereof include an amino group and salts thereof.

The method of producing a medical device in the present invention comprises the steps of placing a substrate that is pretreated by placing the substrate in an alkali solution and heating the substrate at a temperature ranging from 50° C. to 100° C., in a solution containing a hydrophilic polymer having an acidic group and a hydroxyalkyl group, and an organic acid, and heating the pretreated substrate at a temperature ranging from 50° C. to 100° C.

The method of producing a medical device in the present invention preferably comprises a step of pretreating a substrate by placing the substrate in an alkali solution at a temperature ranging from 50° C. to 100° C.; and a step of placing the pretreated substrate in a solution containing a hydrophilic polymer having an acidic group and a hydroxyalkyl group, and an organic acid and heating the pretreated substrate at a temperature ranging from 50° C. to 100° C.

The range of the initial pH of the solution containing a hydrophilic polymer and an organic acid is preferably within a range from 2.0 to 6.0 since the solution shows no turbidity, and a medical device having good transparency can be obtained. The initial pH is more preferably 2.1 or higher, still more preferably 2.2 or higher, yet more preferably 2.4 or higher, and particularly preferably 2.5 or higher. The initial pH is more preferably 5.5 or lower, still more preferably 4.5 or lower, and yet more preferably 4.0 or lower.

When the initial pH is 2.0 or higher, the solution is less likely to show a turbid. No turbid generated in the solution would result in a tendency that the surface of the obtained medical device shows high water wettability and lubricity, and thus is preferable. An initial pH of 6.0 or less would not result in decrease in the water wettability and lubricity of the surface of the obtained medical device, and thus is preferable.

When the substrate is a material containing a silicon atom, the initial pH of the solution containing a hydrophilic polymer is preferably 3.9 or less, more preferably 3.7 or less, and still more preferably 3.5 or less because excellent water wettability and lubricity can be imparted to the substrate. When the substrate is a material containing no silicon atom, the initial pH is preferably 4.5 or less, more preferably 4.3 or less, and still more preferably 4.0 or less.

The pH of the solution can be measured using a pH meter (e.g., pH meter Eutech pH 2700 (Eutech Instruments)). Here, the pH of a solution containing a hydrophilic polymer and an organic acid means the pH value measured after adding all the hydrophilic polymer and organic acid to the solution, followed by stirring at room temperature (20 to 25° C.) for 30 minutes with a rotor to make the solution uniform, and before placing a substrate and heating the substrate. In the present invention, the pH value is rounded off to one decimal place.

The pH of a solution containing a hydrophilic polymer and an organic acid can change when a heating operation is performed. The pH of the solution after a heating operation is preferably from 2.0 to 6.0. The pH after heating is more preferably 2.1 or higher, still more preferably 2.2 or higher, and particularly preferably 2.3 or higher. The pH after heating is more preferably 5.9 or lower, still more preferably 5.5 or lower, yet more preferably 5.0 or lower, and particularly preferably 4.8 or lower. When the pH of the solution after a heating operation is in the above range, an appropriate pH condition can be maintained during the heating operation, which results in achieving suitable physical properties of the obtained medical device. After the heating operation according to the present invention to modify the surface of the substrate used in the medical device, the pH can be adjusted, for example, by performing a neutralization treatment or adding water. The pH of the solution after performing the heating operation as used herein is the pH before performing such pH adjustment.

Preferred examples of a solvent of the solution containing a hydrophilic polymer and an organic acid include water. The pH of the solution can be adjusted by adding an acid to the solution containing a hydrophilic polymer. Preferred specific examples of the acid include organic acids such as acetic acid, citric acid, formic acid, ascorbic acid, trifluoromethanesulfonic acid, and methanesulfonic acid; and inorganic acids such as nitric acid, sulfuric acid, phosphoric acid, and hydrochloric acid. Of these, at least an organic acid is used in the present invention, from the viewpoint of the facts that it is easy to obtain a more excellent hydrophilic surface, the safety to a living body is high, and it is easy to handle. Of these organic acids, an acid selected from acetic acid, citric acid, formic acid, and ascorbic acid is preferable; and citric acid or ascorbic acid is more preferable. In addition, an inorganic acid may be used in combination. Of these inorganic acids, sulfuric acid is preferable, from the viewpoints of non-volatility, odorless, and easy to handle.

Since it becomes easy to finely adjust the pH, and the substrate is less likely to become turbid when the substrate is a material containing a hydrophobic component, a buffer is preferably added to the solution.

It is possible to use, as the buffer, an arbitrary known physiologically compatible buffer. Preferred examples of the buffer in the present invention are as follows: boric acid, borates (e.g., sodium borate), citric acid, citrates (e.g., potassium citrate), bicarbonates (e.g., sodium bicarbonate), phosphate buffers (e.g., $Na_2HPO_4$, $NaH_2PO_4$, and $KH_2PO_4$), TRIS (tris(hydroxymethyl)aminomethane), 2-bis(2-hydroxyethyl)amino-2-(hydroxymethyl)-1,3-propanediol, bis-aminopolyol, triethanolamine, ACES (N-(2-acetamide)-2-aminoethanesulfonic acid). BES (N,N-bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N-bis(2-ethanesulfonic acid)), TES (N-[tris(hydroxymethyl)methyl]-2-aminoethanesulfonic acid), and salts thereof.

The buffer is used in an amount required to be effective for achieving a desired pH. The amount of the buffer in the solution is preferably from 0.001% by mass to 2% by mass, more preferably 0.01% by mass to 1% by mass, and still more preferably 0.05% by mass to 0.30% by mass. The amount may be in a range combining any of the upper limits described above and any of the lower limits described above.

Examples of the method of heating in the step where the solution containing a hydrophilic polymer and an organic acid is heated at a temperature ranging from 50° C. to 100° C. include a heating method (hot air), a high-pressure steam sterilization method, irradiation with electromagnetic waves (γ ray, microwave, etc.), a dry heat method, and a flame method. From the viewpoint of the water wettability, lubricity, and shortening of the production process, a heating method (hot air) is most preferable. A constant-temperature oven or a hot air circulating oven is preferably used as the apparatus.

The heating temperature in the step of heating the solution containing a hydrophilic polymer and an organic acid after the pretreatment is within a range from 50° C. to 100° C. from the viewpoint of obtaining a medical device surface exhibiting good water wettability and lubricity, and exerting less influence on the strength of the medical device itself. The heating temperature is more preferably 51° C. or higher, still more preferably 55° C. or higher, and particularly preferably 60° C. or higher. The heating temperature is more preferably 99° C. or lower, still more preferably 95° C. or lower, and particularly preferably 90° C. or lower.

The heating time period is preferably from 5 minutes to 600 minutes, because too short time period results in failure to obtain a medical device surface exhibiting good water wettability and lubricity, and too long time period affects the strength of the medical device itself. The heating time period is more preferably 10 minutes or longer, and more preferably 15 minutes or longer. The heating time period is more preferably 400 minutes or shorter, and more preferably 300 minutes or shorter.

The medical device obtained by the method of the present invention preferably has a hydrophilic polymer layer existing on one entire surface of the substrate surfaces, depending on the application. In the case where the substrate has a two-dimensional shape that has no or, if any, negligible thickness, a hydrophilic polymer layer preferably exists on one entire surface of the substrate surfaces. More preferably, a hydrophilic polymer layer exits on all the surfaces of the substrate.

To enable production by a simple process regardless of whether the substrate is hydrated or nonhydrated, the hydrophilic polymer contained in the hydrophilic polymer layer preferably does not have any covalent bond with the substrate. The absence of a covalent bond is determined by the absence of chemically reactive group. Specific examples of the chemically reactive group include, but are not limited to, an azetidinium group, an epoxy group, an isocyanate group, an aziridine group, an azlactones group, and combinations thereof. The hydrophilic polymer is preferably bound to the substrate via one or more selected from hydrogen bond, ionic bond, van der Waals bond, hydrophobic bond, complex formation.

The thickness of the hydrophilic polymer layer is 1 nm or more and less than 100 nm in observation of a cross section of the medical device in a dry state using a transmission electron microscope. When the thickness is in the above range, functions such as water wettability and lubricity are likely to be exhibited. The thickness is more preferably 5 nm or more, and still more preferably 10 nm or more. The thickness is more preferably 95 nm or less, still more preferably 90 nm or less, and particularly preferably 85 nm or less. When the thickness of the hydrophilic polymer layer is less than 100 nm, the hydrophilic polymer layer is excellent in water wettability and lubricity. For example, when the hydrophilic polymer layer is used in a medical device such as an ophthalmic lens, refraction of light for focusing on the retina is not disturbed and poor visibility is less likely to occur.

The thickness of the hydrophilic polymer layer in observation of a cross section of the device in a hydrated and frozen state (hereinafter, referred to as "frozen") using a scanning transmission electron microscope is preferably 1 nm or more and less than 100 nm, because functions such as water wettability and lubricity are likely to be exhibited. The thickness is more preferably 5 nm or more, still more preferably 10 nm or more, and particularly preferably 15 nm or more. The thickness is more preferably 95 nm or less, still more preferably 90 nm or less, and particularly preferably 85 nm or less. The thickness of the frozen hydrophilic polymer layer can be measured by scanning transmission electron microscopy using Cryo-Transfer Holder.

It is not preferable that the thickness of the frozen polymer layer is 100 nm or more, because, for example, refraction of light for focusing on the retina is disturbed and poor visibility is likely to occur when the frozen polymer layer is used in a medical device such as an ophthalmic lens.

The hydrophilic polymer layer is preferably in a state separated into two or more layers or two or more phases.

At least a portion of the hydrophilic polymer layer preferably exists in a mixed state with the substrate. The state where the hydrophilic polymer layer is mixed with the substrate can be determined by comparison of the cross-sectional structures of the substrates before and after the formation of the hydrophilic polymer layer, and by detection of elements derived from the substrate in at least a portion of the hydrophilic polymer layer, when a cross section of the medical device is observed using observation means capable of performing elemental analysis or composition analysis, such as scanning transmission electron microscopy, electron energy-loss spectroscopy, energy dispersive X-ray spectroscopy, or time-of-flight secondary ion mass spectrometry. By mixing the hydrophilic polymer layer with the substrate, the hydrophilic polymer can be firmly fixed to the substrate.

When at least a portion of the hydrophilic polymer layer exists in a mixed state with the substrate, it is preferable that a two-layer structure comprising a "layer in which at least a portion of the hydrophilic polymer layer is mixed with the substrate" (hereinafter referred to as a "mixed layer") and a "layer made of the hydrophilic polymer" (hereinafter referred to as a "single laver") is observed. The thickness of the mixed layer is preferably 3% or more, more preferably 5% or more, and still more preferably 10% or more, based on the total thickness of the mixed layer and the single layer. The thickness of the mixed layer is preferably 98% or less, more preferably 95% or less, still more preferably 90% or less, and particularly preferably 80% or less, based on the total thickness of the mixed layer and the single layer. Too small percentage of the thickness of the mixed layer results in insufficient mixing of the hydrophilic polymer and the substrate, and thus is not preferable. Too large percentage of the thickness of the mixed layer may cause insufficient properties of the hydrophilic polymer to be exerted, and thus is not preferable.

When the medical device in the present invention is, for example, a medical device which is used by being attached to a surface of a living body or an ophthalmic device such as an ophthalmic lens, the liquid film retention time on the surface of the medical device is preferably longer from the viewpoints of preventing it from sticking to the skin of the user and preventing it from sticking to the cornea of the wearer. Here, the liquid film retention time in the present invention refers to the time period during which the liquid film on the surface of the medical device is retained without breaking when the medical device immersed in a phosphate buffer solution is pulled up from the solution, and held in the air such that the surface is vertical. The phrase "liquid film disappears" refers to a state where the liquid film on the surface of the medical device can no longer keep its shape, leading to a phenomenon that the surface of the medical device repels water, so that the surface of the medical device is no longer completely covered by the liquid film. The liquid film retention time is preferably 10 seconds or more, more preferably 15 seconds or more, and particularly preferably 20 seconds or more.

The medical device of the present invention preferably has a long liquid film retention time of the surface of the medical device after sterilization. Long liquid film retention time of the surface of the medical device after sterilization means, in addition to guarantee of safety, the hydrophilic polymer strongly immobilized to the substrate even after sterilization, which is an indicator of durability of the water wettability of the medical device. The method of sterilization may be, for example, autoclaving, dry heat sterilization, burning sterilization, boiling sterilization, free-flowing steam sterilization, ethylene oxide gas sterilization, Y-ray sterilization, or UV-ray sterilization. Autoclaving, ethylene oxide gas sterilization, and Y-ray sterilization are preferable; and autoclaving and ethylene oxide gas sterilization are more preferable; and autoclaving is still more preferable, from the viewpoint of simplicity. When the medical device of the present invention is an ophthalmic device such as an ophthalmic lens, and is stored in a solution, the solution used for storage is not particularly limited and is preferably a buffer solution. The above-mentioned substances can be used as the buffer.

When the medical device of the present invention is used, for example, with insertion into a living body, it is preferred that the surface of the medical device have an excellent lubricity. As an indicator of lubricity, the frictional coefficient, as measured by the method shown in the examples herein, is preferably smaller. The frictional coefficient is preferably 0.7 or less, more preferably 0.5 or less, and particularly preferably 0.3 or less. Since extremely small friction tends to make handling when removing and wearing difficult, the frictional coefficient is preferably 0.001 or more, and more preferably 0.002 or more.

In the method of producing a medical device of the present invention, the percent change between the moisture content of the substrate before the alkali pretreatment and the moisture content of the medical device obtained after the heating step is preferably 10 percentage points or less. Here, the percent change in the moisture content (percentage point) means a difference between the moisture content (% by mass) of the resulting medical device and the moisture content (% by mass) of the substrate as a raw material of the medical device.

The percent change in the moisture content when the medical device of the present invention is used, for example, in an ophthalmic device such as an ophthalmic lens, is preferably 15 percentage points or less, more preferably 10 percentage points or less, and particularly preferably 8 percentage points or less, from the viewpoint of preventing poor visibility and deformation caused by distortion of the refractive index due to the increase in moisture content. Details of the measurement method will be described later.

The percent change in the size between the substrate before the alkali pretreatment and the medical device obtained after the heating step, for example, in the case for use in an ophthalmic device such as an ophthalmic lens, is preferably 10% or less, more preferably 8 or less, and particularly preferably 5% or less, from the viewpoint of preventing corneal injury caused by deformation. Details of the measurement method will be described later.

The percent change in the tensile elastic modulus between the substrate before the alkali pretreatment and the medical device obtained after the heating step is preferably 15% or less, more preferably 14% or less, and particularly preferably 13% or less. Too large percent change in the tensile elastic modulus may lead to deformation and poor tactile sensation, and thus is not preferable. Details of the measurement method will be described later.

The antifouling properties of the medical device of the present invention can be evaluated based on deposition of mucin or lipid (methyl palmitate). The smaller the deposition amount from the evaluation, the more tactile sensation is excellent and bacterial propagation risk is reduced, which is preferable. The amount of mucin deposition is preferably 10 $\mu g/cm^2$ or less, more preferably 8 $\mu g/cm^2$ or less, and particularly preferably 6 $\mu g/cm^2$ or less. Details of the measurement method will be described later.

After the above heat treatment, the obtained medical device may be further subjected to other treatments. Examples of the other treatments include a method in which a similar heat treatment is performed in a solution containing a hydrophilic polymer; a method in which a similar heat treatment is performed after changing the solution to a solution not containing a hydrophilic polymer; a method in which radiation is performed; a method in which a Layer-by-Layer treatment (LbL treatment) is performed for coating polymer materials having opposite charges alternately layer by layer; a method in which a crosslinking treatment with metal ions is performed; and a method in which a chemical crosslinking treatment is performed.

However, in light of the idea of the present invention that hydrophilization of a substrate surface can be achieved by a simple method, a treatment is preferably performed without making the production process too complicated.

Radiations used for the above radiation are preferably various ion beams, electron beams, positron beams, X-rays, γ rays, and neutron rays, more preferably electron beams and γ rays, and most preferably γ rays.

As the above LbL treatment, for example, a treatment using an acidic polymer and a basic polymer as disclosed in WO2013/024800 can be used.

As metal ions used in the above crosslinking treatment with metal ions, various metal ions are preferable, and monovalent and divalent metal ions are more preferable, and divalent metal ions are most preferable. Alternatively, a chelate complex may be used.

As the above chemical crosslinking treatment, for example, a crosslinking treatment formed by a reaction between an epoxide group and a carboxy group, or a crosslinking treatment formed between known appropriate acidic hydrophilic polymers having a hydroxy group, as disclosed in JP 2014-533381 A, can be used.

In the above method in which a similar heat treatment is performed after changing the solution to a solution not containing a hydrophilic polymer, the solution not containing a hydrophilic polymer is not particularly limited and is preferably a buffer solution. The above-mentioned substances can be used as the buffer.

The pH of the buffer solution is preferably within a physiologically acceptable range of 6.3 to 7.8. The pH of the buffer solution is preferably 6.5 or higher, and more preferably 6.8 or higher. The pH of the buffer solution is preferably 7.6 or lower, and more preferably 7.4 or lower.

EXAMPLES

The present invention will be described in more detail by way of the examples, but the present invention is not limited thereto. First, analytical methods and evaluation methods will be shown. The liquid film retention time after sterilization shown below is an index representing the durability of the water wettability of the medical device.

<Water Wettability after Sterilization (Liquid Film Retention Time)>

A medical device was sterilized in phosphate buffer using an autoclave at 121° C. for 30 minutes, and then allowed to cool to room temperature (20° C. to 23° C.). Thereafter, the medical device was pulled up from the phosphate buffer solution and held in the air. The time period for which the liquid film on the surface was retained was visually observed, and the average from N=3 was evaluated according to the following criteria:

A: The liquid film on the surface was retained for 20 seconds or more;
B: The liquid film on the surface disappeared after 15 seconds or more and less than 20 seconds:
C: The liquid film on the surface disappeared after 10 seconds or more and less than 15 seconds:
D: The liquid film on the surface disappeared after 1 second or more and less than 10 seconds;
E: The liquid film on the surface instantly disappeared (after less than 1 second).

<Moisture Content of Substrate and Medical Device>

A substrate before the alkali pretreatment was immersed in a phosphate buffer solution and left to stand at room temperature for 24 hours or more. The substrate was pulled out from the phosphate buffer solution. After wiping off the surface moisture with a wiping cloth ("Kimwipes" (registered trademark) manufactured by Nippon Paper Crecia Co., Ltd.), the mass (Ww) of the substrate was measured. Thereafter, the substrate was dried in a vacuum dryer at 40° C. for 2 hours and the mass (Wd) was measured. From the mass, the moisture content of the substrate was calculated according to the following formula (1). The case where the obtained value was less than 1% was determined as below the measurement limit, and the column in the table was filled with "less than 1%". The average value from N=3 was regarded as the moisture content. The medical device obtained after the heating step was also pulled out from the solution. After wiping off the surface moisture with a wiping cloth ("Kimwipes" (registered trademark) manufactured by Nippon Paper Crecia Co., Ltd.), the moisture content was measured in the same manner.

$$\text{Moisture content (\%) of substrate} = 100 \times (Ww - Wd)/Ww \quad \text{Formula (1)}$$

<Percent Change in Moisture Content of Substrate and Medical Device>

From the measurement results of the moisture content of the substrate and the medical device described above, the percent change in the moisture content was calculated according to the following formula (2):

$$\text{Percent change in moisture content of substrate and medical device (percentage point)} = \text{moisture content of medical device (\% by mass)} - \text{moisture content of substrate (\% by mass)} \quad \text{Formula (2)}.$$

<Amount of Deposited Lipid>

In a 20-cc screw tube, 0.03 g of methyl palmitate, 10 g of pure water, and one sample in a shape of contact lens were placed. The screw tube was shaken for 3 hours under the conditions at 37° C. and 165 rpm. After shaking, the sample in the screw tube was scrubbed with tap water at 40° C. and a household liquid detergent ("Mama Lemon (registered trademark)" manufactured by Lion Corporation). The washed sample was placed in a screw tube containing a phosphate buffer solution and stored in a refrigerator at 4° C. overnight. Thereafter, the sample was visually observed, and if the turbid portion existed, it was judged that methyl palmitate was deposited. The percentage of the area of the portion in which methyl palmitate was deposited to the entire surface of the sample was determined.

<Tensile Elastic Modulus>

A test piece having a width (minimum portion) of 5 mm and a length of 14 mm was cut out from a substrate having a contact lens or sheet shape using a prescribed punching die. Using the test piece, a tensile test was performed using Tensilon Model RTG-1210 manufactured by A&D Company, Limited. The pulling rate was 100 mm/min and the distance between grips (initial) was 5 mm. Measurements were made on both the substrate before the alkali pretreatment and the medical device obtained after the heating step. Measurements were made with N=8 and the average of N=6 excluding the maximum value and the minimum value was regarded as the tensile elastic modulus.

<Percent Change in Tensile Elastic Modulus of Substrate and Medical Device>

From the measurement results of the tensile elastic modulus of the substrate and the medical device described above, calculation was performed according to the following formula (3). The average of N=6 was regarded as the percent change in tensile elastic modulus before and after heating.

Percent change in tensile elastic modulus of substrate and medical device (%)=(tensile elastic modulus of medical device−tensile elastic modulus of substrate)/tensile elastic modulus of substrate×100     Formula (3)

<Size>

The diameters of substrates (N=3) having a contact lens or sheet shape were measured and the average was regarded as the size of a substrate. The size of the medical device obtained after the heating step was also measured in the same manner.

<Percent Change in Size of Substrate and Medical Device>

From the measurement results of the size of the substrate and the medical device described above, calculation was performed according to the following formula (4). The average value of N=3 was regarded as the percent change in the size before and after heating.

Percent change (%) in size of substrate and medical device=(Size of medical device−Size of substrate)/Size of substrate×100     Formula (4)

<Amount of Deposited Mucin>

A test piece having a width (minimum portion) of 5 mm and a length of 14 mm was cut out from a sample having a contact lens shape using a prescribed punching die. Mucin, Bovine Submaxillary Gland (Catalog Number: 499643) manufactured by Calbiochem was used as mucin. The test piece was immersed in an aqueous solution of 0.1% mucin at 37° C. for 20 hours. Then, the amount of mucin deposited on the sample was determined by a BCA (bicinchoninic acid) protein assay method. The average value of N=3 was regarded as the amount of deposited mucin.

<Frictional Coefficient>

The frictional coefficient of the surface of a medical device that is wet with phosphate buffer was measured under the following conditions in N=3, and the average value was regarded as the frictional coefficient.

Equipment: Friction Tester KES-SE (Kato Tech Co., Ltd.)
Friction SENS: H
Measurement SPEED: 2-1 mm/sec
Friction load: 44 g.

<Measurement of Molecular Weight>

The molecular weight of a hydrophilic polymer was measured under the following conditions.

Equipment: Prominence GPC system manufactured by Shimadzu Corporation
Pump: LC-20AD
Autosampler: SIL-20AHT
Column oven: CTO-20A
Detector: RID-10A
Column: GMPWXL (inner diameter: 7.8 mm 30 cm, particle size: 13 μm) manufactured by Tosoh Corporation
Solvent: water/methanol=1/1 (adding 0.1 N lithium nitrate)
Flow rate: 0.5 mL/min
Measurement time: 30 minutes
Sample concentration: 0.1 to 0.3% by mass
Sample injection amount: 100 μL
Standard sample: Polyethylene oxide standard sample manufactured by Agilent Technologies, Inc. (0.1 kD to 1258 kD)

<pH Measurement Method>

The pH of a solution was measured using a pH meter. Eutech pH 2700 (manufactured by Eutech Instruments Pte Ltd). In the table, the pH before heat treatment of a solution containing a hydrophilic polymer and an organic acid was measured by adding all the hydrophilic polymer and the organic acid to the solution mentioned in each Example and Comparative Example, followed by stirring at room temperature (20 to 25° C.) for 30 minutes with a rotor to make the solution uniform. In the table, "pH after heat treatment" is the pH measured immediately after the solution was cooled to room temperature (20 to 25° C.) after a heat treatment was performed once.

<Film Thicknesses of Hydrophilic Polymer Layer>

The film thickness was measured by observing a cross section of a medical device in a dry state using a transmission electron microscope. With changing the place three times, the thickness was measured once for each field of view, and the average of the film thicknesses at the three places was mentioned.

Equipment: Transmission electron microscope
Conditions: Acceleration voltage 100 kV
Sample preparation: Samples were prepared by ultramicrotomy using $RuO_4$ staining. When it is difficult to discriminate between a substrate and a hydrophilic polymer layer, the sample may be stained with $OsO_4$. In this Example, when the substrate is a silicone hydrogel-based or silicone-based substrate, the sample was stained with $RuO_4$. For preparation of ultrathin sections, an ultramicrotome was used.

Production Example 1

After preparing 28 parts by mass of a polydimethylsiloxane having methacryloyl groups at both ends represented by the formula (M1) (FM 7726, JNC Corporation, Mw: 30,000), 7 parts by mass of a silicone monomer represented by the formula (M2) (FM 0721, JNC Corporation, Mw: 5,000). 57.9 parts by mass of trifluoroethyl acrylate ("Viscoat" (registered trademark) 3F, Osaka Organic Chemical Industry Ltd.), 7 parts by mass of 2-ethylhexyl acrylate (Tokyo Chemical Industry Co., Ltd.), and 0.1 parts by mass of dimethylaminoethyl acrylate (Kohjin Co., Ltd.), preparing 5,000 ppm of a photoinitiator "IRGACURE" (registered trademark) 819 (NAGASE & CO., LTD.), 5,000 ppm of a UV absorber (RUVA-93, Otsuka Chemical Co., Ltd.), and 100 ppm of a colorant (RB 246, Arran chemical) based on the total amount of these monomers, and preparing 10 parts by mass of t-amyl alcohol based on 100 parts by mass of the total amount of these monomers, all components were mixed with stirring. The stirred mixture was filtered through a membrane filter (pore diameter: 0.45 μm) to remove insoluble substances to obtain a monomer mixture.

The above monomer mixture was poured into a contact lens mold made of a transparent resin (material on base curve side: polypropylene, material on front curve side: polypropylene) and then polymerized by irradiation with light (wavelength 405 nm (±5 nm), illuminance: 0 to 0.7 mW/cm², for 30 minutes) to obtain a molded body made of a low water content soft material having a silicon atom.

After the polymerization, the molded body thus obtained was immersed in an aqueous solution of 100% by mass isopropyl alcohol at 60° C. for 1.5 hours together with the mold from which a front curve and a base curve were released, and then a molded body having a contact lens shape was removed from the mold. The molded body thus obtained was immersed in a large excess amount of an aqueous solution of 100% by mass isopropyl alcohol maintained at 60° C. for 2 hours to extract impurities such as residual monomers. Thereafter, the molded body was dried at room temperature (20° C. to 23° C.) for 12 hours to obtain a substrate.

[Chemcial Formula 1]

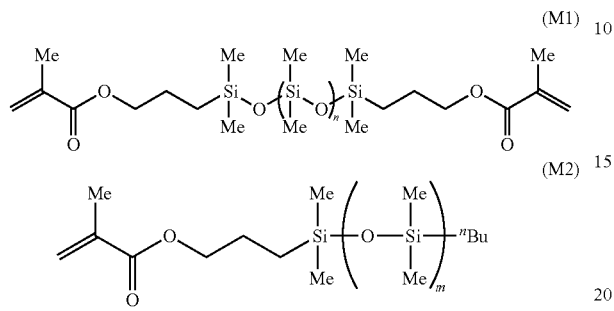

<Phosphate Buffer>

The phosphate buffer solutions used in the processes of the following Examples and Comparative Examples and the above-mentioned measurements are aqueous solutions having the following compositions. In the composition described below, EDTA2Na represents disodium dihydrogen ethylenediaminetetraacetate.

KCl 0.2 g/L
$KH_2PO_4$ 0.2 g/L
NaCl 8.0 g/L
$Na_2HPO_4$ 1.19 g/L
EDTA2Na 0.5 g/L

Example 1

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 mol/L aqueous NaOH solution (pH12.0) and heating it using a constant-temperature oven at 90° C. for 15 minutes. The pretreated substrate was immersed in a solution (coat solution) containing 0.6% by mass of an acrylic acid/2-hydroxyethyl methacrylate/N,N-dimethyl acrylamide copolymer (molar ratio in copolymerization: 1/1/2, Mw: 430,000, manufactured by Osaka Organic Chemical Industry Ltd.) in phosphate buffer with the pH adjusted to 3.4 with citric acid, and left to stand at room temperature for 15 minutes. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 21

The substrate in Production Example 1 was used as a substrate. The substrate was pretreated by immersing it in 0.9 mol/L aqueous NaOH solution (pH12.4) and heating it using a constant-temperature oven at 90° C. for 30 minutes. The pretreated substrate was immersed in a solution (coat solution) containing 0.6% by mass of an acrylic acid/2-hydroxyethyl methacrylate/N,N-dimethyl acrylamide copolymer (molar ratio in copolymerization: 1/1/2, Mw: 430,000, manufactured by Osaka Organic Chemical Industry Ltd.) in phosphate buffer with the pH adjusted to 3.4 with citric acid, and left to stand at room temperature overnight. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 3

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 mol/L aqueous NaOH solution (pH12.0) and heating it using a constant-temperature oven at 90° C. for 15 minutes. The pretreated substrate was immersed in a solution (coat solution) containing 0.6% by mass of an acrylic acid/2-hydroxyethyl methacrylate copolymer (molar ratio in copolymerization: 1/2, Mw: 400,000, manufactured by Osaka Organic Chemical Industry Ltd.) in phosphate buffer with the pH adjusted to 3.4 with citric acid, and left to stand at room temperature for 15 minutes. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 4

The substrate in Production Example 1 was used as a substrate. The substrate was pretreated by immersing it in 0.9 mol/L aqueous NaOH solution (pH12.4) and heating it using a constant-temperature oven at 90° C. for 30 minutes. The pretreated substrate was immersed in a solution (coat solution) containing 0.6% by mass of an acrylic acid/2-hydroxyethyl methacrylate copolymer (molar ratio in copolymerization: 1/2, Mw: 400,000, manufactured by Osaka Organic Chemical Industry Ltd.) in phosphate buffer with the pH adjusted to 3.4 with citric acid, and left to stand at room temperature overnight. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 51

A commercially available hydrogel lens containing 2-hydroxyethyl methacrylate as a main component "1day Acuvue (registered trademark)" (etafilcon A, manufactured by Johnson&Johnson) was used as a substrate. The substrate was pretreated by immersing it in 0.4 mol/L aqueous NaOH solution (pH12.0) and heating it using a constant-temperature oven at 80° C. for 15 minutes. The pretreated substrate was immersed in a solution (coat solution) containing 0.6% by mass of an acrylic acid/2-hydroxyethyl methacrylate/N,N-dimethyl acrylamide copolymer (molar ratio in copolymerization: 1/1/2, Mw: 430,000, manufactured by Osaka Organic Chemical Industry Ltd.) in phosphate buffer with the pH adjusted to 3.4 with citric acid, and left to stand at room temperature for 15 minutes. The substrate was removed from the coat solution, immersed in a fresh coat solution with the same composition, and heated using a constant-temperature oven at 80° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 6

The substrate in Production Example 1 was used as a substrate. The substrate was pretreated by immersing it in 0.9 mol/L aqueous KOH solution (pH12.4) and heating it using a constant-temperature oven at 90° C. for 15 minutes. The pretreated substrate was immersed in a solution (coat solution) containing 0.6% by mass of an acrylic acid/2-hydroxyethyl methacrylate copolymer (molar ratio in copolymerization: 1/2, Mw: 400,000, manufactured by Osaka Organic Chemical Industry Ltd.) in phosphate buffer with the pH adjusted to 3.0 with citric acid, and left to stand at room temperature overnight. The substrate was removed from the coat solution, immersed in a fresh coat solution with the same composition, and heated using a constant-temperature oven at 75° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 7

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 mol/L aqueous KOH solution (pH12.0) and heating it using a constant-temperature oven at 90° C. for 15 minutes. The pretreated substrate was immersed in a solution (coat solution) containing 0.6% by mass of an acrylic acid/2-hydroxyethyl methacrylate/N,N-dimethyl acrylamide copolymer (molar ratio in copolymerization: 1/1/2, Mw: 200,000, manufactured by Osaka Organic Chemical Industry Ltd.) in phosphate buffer with the pH adjusted to 3.3 with citric acid, and left to stand at room temperature for 15 minutes. The substrate was removed from the coat solution, transferred to a fresh coat solution with the same composition, and heated using a constant-temperature oven at 80° C. for 45 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 81

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 molt aqueous NaOH solution (pH12.0) and heating it using a constant-temperature oven at 90° C. for 15 minutes. The pretreated substrate was immersed in a solution (coat solution) containing 0.6% by mass of an acrylic acid/2-hydroxyethyl methacrylate/N,N-dimethyl acrylamide copolymer (molar ratio in copolymerization: 2/2/1, Mw: 400,000, manufactured by Osaka Organic Chemical Industry Ltd.) in phosphate buffer with the pH adjusted to 3.4 with citric acid, and left to stand at room temperature for 15 minutes. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 9

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 mol/L aqueous NaOH solution (pH12.0) and heating it using a constant-temperature oven at 90° C. for 15 minutes. The pretreated substrate was immersed in a solution (coat solution) containing 0.6% by mass of an acrylic acid/2-hydroxyethyl methacrylate/N,N-dimethyl acrylamide copolymer (molar ratio in copolymerization: 3/5/2, Mw: 400,000, manufactured by Osaka Organic Chemical Industry Ltd.) in phosphate buffer with the pH adjusted to 3.4 with citric acid, and left to stand at room temperature for 15 minutes. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 10

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 mol/L aqueous NaOH solution (pH12.0) and heating it using a constant-temperature oven at 90° C. for 15 minutes. The pretreated substrate was immersed in a solution (coat solution) containing 0.6% by mass of an acrylic acid/2-hydroxyethyl methacrylate copolymer (molar ratio in copolymerization: 2/3, Mw: 300,000, manufactured by Osaka Organic Chemical Industry Ltd.) in phosphate buffer with the pH adjusted to 3.2 with citric acid, and left to stand at room temperature for 15 minutes. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes.

The results obtained by evaluation of the obtained medical device using the above method are shown in Tables 1 to 3.

Example 11

The substrate in Production Example 1 was used as a substrate. The substrate was pretreated by immersing it in 0.6 mol/L aqueous NaOH solution (pH12.1) and heating it using a constant-temperature oven at 70° C. for 60 minutes. The pretreated substrate was transferred to a solution (coat solution) containing 0.2% by mass of an acrylic acid/2-hydroxyethyl methacrylate/N,N-dimethyl acrylamide copolymer (molar ratio in copolymerization: 1/1/2, Mw: 550,000, manufactured by Osaka Organic Chemical Industry Ltd.) in phosphate buffer with the pH adjusted to 3.3 with citric acid, and heated using an autoclave at 70° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 12

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.6 mol/L aqueous NaOH solution (pH12.1) and heating it using a constant-temperature oven at 60° C. for 90 minutes. The pretreated substrate was placed in a solution (coat solution) containing 0.2% by mass of an acrylic acid/2-hydroxyethyl methacrylate/N,N-dimethyl acrylamide copolymer (molar ratio in copolymerization: 1/1/2, Mw: 550,000, manufactured by Osaka Organic Chemical Industry Ltd.) in phosphate buffer with the pH adjusted to 3.3 with citric acid, and heated using an autoclave at 70° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Example 131

A commercially available hydrogel lens containing 2-hydroxyethyl methacrylate as a main component "1day Acuvue (registered trademark)" (etafilcon A, manufactured by Johnson&Johnson) was used as a substrate. The substrate was pretreated by immersing it in 0.6 molt aqueous NaOH solution (pH12.1) and heating it using a constant-temperature oven at 50° C. for 100 minutes. The pretreated substrate was placed in a solution (coat solution) containing 0.2% by mass of an acrylic acid/2-hydroxyethyl methacrylate/N,N-dimethyl acrylamide copolymer (molar ratio in copolymerization: 1/1/2, Mw: 550,000, manufactured by Osaka Organic Chemical Industry Ltd.) in phosphate buffer with the pH adjusted to 3.3 with citric acid, and heated using an autoclave at 70° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

TABLE 1

| | Substrate | Moisture content of substrate (% by mass) | Alkali and concentration of solution thereof | Hydrophilic polymer and concentration of solution thereof | pH before heat treatment | pH after heat treatment |
|---|---|---|---|---|---|---|
| Example 1 | "1dayAcuvueOasys (registered trademark)" | 38.0 | 0.4 mol/L aqueous NaOH solution | 0.6% by mass acrylic acid/ 2-hydroxyethyl methacrylate/ N,N-dimethyl acrylamide copolymer | 3.4 | 3.7 |
| Example 2 | Production Example 1 | <1 | 0.9 mol/L aqueous NaOH solution | 0.6% by mass acrylic acid/ 2-hydroxyethyl methacrylate/ N,N-dimethyl acrylamide copolymer | 3.4 | 3.9 |
| Example 3 | "1dayAcuvueOasys" (registered trademark) | 38.0 | 0.4 mol/L aqueous NaOH solution | 0.6% by mass acrylic acid/ 2-hydroxyethyl methacrylate copolymer | 3.4 | 3.6 |
| Example 4 | Production Example 1 | <1 | 0.9 mol/L aqueous NaOH solution | 0.6% by mass acrylic acid/ 2-hydroxyethyl methacrylate copolymer | 3.4 | 3.8 |
| Example 5 | "1day Acuvue" (registered trademark) | 58.0 | 0.4 mol/L aqueous NaOH solution | 0.6% by mass acrylic acid/ 2-hydroxyethyl methacrylate/ N,N-dimethyl acrylamide copolymer | 3.4 | 3.6 |
| Example 6 | Production Example 1 | <1 | 0.9 mol/L aqueous KOH solution | 0.6% by mass acrylic acid/ 2-hydroxyethyl | 3.0 | 3.2 |

TABLE 1-continued

| | Substrate | Moisture content of substrate (% by mass) | Alkali and concentration of solution thereof | Hydrophilic polymer and concentration of solution thereof | pH before heat treatment | pH after heat treatment |
|---|---|---|---|---|---|---|
| Example 7 | "1dayAcuvueOasys" (registered trademark) | 38.0 | 0.4 mol/L aqueous KOH solution | methacrylate copolymer 0.6% by mass acrylic acid/ 2-hydroxyethyl methacrylate/ N,N-dimethyl acrylamide copolymer | 3.3 | 3.5 |
| Example 8 | "1dayAcuvueOasys" (registered trademark) | 38.0 | 0.4 mol/L aqueous NaOH solution | 0.6% by mass acrylic acid/ 2-hydroxyethyl methacrylate/ N,N-dimethyl acrylamide copolymer | 3.4 | 3.7 |
| Example 9 | "1dayAcuvueOasys" (registered trademark) | 38.0 | 0.4 mol/L aqueous NaOH solution | 0.6% by mass acrylic acid/ 2-hydroxyethyl methacrylate/ N,N-dimethyl acrylamide copolymer | 3.4 | 3.8 |
| Example 10 | "1dayAcuvueOasys" (registered trademark) | 38.0 | 0.4 mol/L aqueous NaOH solution | 0.6% by mass acrylic acid/ 2-hydroxyethyl methacrylate copolymer | 3.2 | 3.4 |
| Example 11 | Production Example 1 | <1 | 0.6 mol/L aqueous NaOH solution | 0.2% by mass acrylic acid/ 2-hydroxyethyl methacrylate/ N,N-dimethyl acrylamide copolymer | 3.3 | 3.9 |
| Example 12 | "1dayAcuvueOasys" (registered trademark) | 38.0 | 0.6 mol/L aqueous NaOH solution | 0.2% by mass acrylic acid/ 2-hydroxyethyl methacrylate/ N,N-dimethyl acrylamide copolymer | 3.3 | 3.8 |
| Example 13 | "1day Acuvue" (registered trademark) | 58.0 | 0.6 mol/L aqueous NaOH solution | 0.2% by mass acrylic acid/ 2-hydroxyethyl methacrylate/ N,N-dimethyl acrylamide copolymer | 3.3 | 3.9 |

TABLE 2

| | Liquid film retention time after sterilization (sec) | Frictional coefficient | Amount of mucin deposition (μg/cm$^2$) | Moisture content of medical device (% by mass) | Percent change in moisture content (percentage point) | Thickness of hydrophilic polymer layer(nm) |
|---|---|---|---|---|---|---|
| Example 1 | A (120 sec) | 0.006 | 1.8 | 38.2 | 0.2 | 12 |
| Example 2 | A (25 sec) | 0.008 | 5.3 | 1.2 | 0.2 | 10 |
| Example 3 | A (30 sec) | 0.305 | 2.5 | 38.2 | 0.2 | 10 |
| Example 4 | A (25 sec) | 0.365 | 4.9 | 1.2 | 0.2 | 11 |
| Example 5 | A (120 sec) | 0.010 | 3.9 | 58.3 | 0.3 | 11 |
| Example 6 | A (25 sec) | 0.387 | 4.2 | 1.1 | 0.1 | 9 |
| Example 7 | A (120 sec) | 0.006 | 1.5 | 38.2 | 0.2 | 11 |
| Example 8 | A (120 sec) | 0.009 | 3.2 | 38.2 | 0.2 | 12 |
| Example 9 | A (120 sec) | 0.008 | 3.7 | 38.3 | 0.3 | 11 |
| Example 10 | A (30 sec) | 0.330 | 4 1 | 38.2 | 0.2 | 9 |
| Example 11 | A (25 sec) | 0.010 | 4.0 | 1.2 | 0.2 | 10 |
| Example 12 | A (120 sec) | 0.015 | 4.3 | 38.2 | 0.2 | 12 |
| Example 13 | A (120 sec) | 0.030 | 4.6 | 58.3 | 0.3 | 11 |

TABLE 3

| | Amount of lipid deposition | Tensile elastic modulus of substrate (MPa) | Tensile elastic modulus of medical device (MPa) | Percent change in tensile elastic modulus (%) | Size of substrate (mm) | Size of medical device (mm) | Percent change in size (%) |
|---|---|---|---|---|---|---|---|
| Example 1 | No deposition | 0.70 | 0.73 | 4.3 | 14.20 | 14.28 | 0.56 |
| Example 2 | No deposition | 0.53 | 0.54 | 1.9 | 14.20 | 14.35 | 1.05 |
| Example 3 | No deposition | 0.70 | 0.71 | 1.4 | 14.20 | 14.25 | 0.35 |
| Example 4 | No deposition | 0.53 | 0.55 | 0.2 | 14.20 | 14.30 | 1.26 |
| Example 5 | No deposition | 0.30 | 0.31 | 3.3 | 14.20 | 14.40 | 1.41 |
| Example 6 | No deposition | 0.53 | 0.53 | 1.9 | 14.20 | 14.35 | 1.05 |
| Example 7 | No deposition | 0.70 | 0.71 | 1.4 | 14.20 | 14.27 | 0.49 |
| Example 8 | No deposition | 0.70 | 0.73 | 4.3 | 14.20 | 14.30 | 0.70 |
| Example 9 | No deposition | 0.70 | 0.72 | 2.9 | 14.20 | 14.31 | 0.77 |
| Example 10 | No deposition | 0.70 | 0.71 | 1.4 | 14.20 | 14.29 | 0.63 |
| Example 11 | No deposition | 0.53 | 0.54 | 1.8 | 14.20 | 14.35 | 1.05 |
| Example 12 | No deposition | 0.70 | 0.71 | 1.4 | 14.20 | 14.30 | 0.70 |
| Example 13 | No deposition | 0.30 | 0.31 | 3.3 | 14.20 | 14.39 | 1.3 |

Comparative Example 1

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 molt aqueous NaOH solution (pH12.0) and heating it using a constant-temperature oven at 90° C. for 15 minutes. The pretreated substrate was immersed in a solution (coat solution) containing 0.6% by mass of polyacrylic acid "Sokalan (registered trademark) PA110S" (Mw: 250,000, manufactured by BASF SE) in phosphate buffer with the pH adjusted to 3.4 with citric acid, and left to stand at room temperature for 15 minutes. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 21

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 mol/L aqueous NaOH solution (pH12.0) and heating it using a constant-temperature oven at 50° C. for 10 minutes. The pretreated substrate was immersed in a solution (coat solution) containing 0.6% by mass of an acrylic acid/2-hydroxyethyl methacrylate/N,N-dimethyl acrylamide copolymer (molar ratio in copolymerization: 1/1/2, Mw: 430,000, manufactured by Osaka Organic Chemical Industry Ltd.) in phosphate buffer with the pH adjusted to 3.4 with citric acid, and left to stand at room temperature for 15 minutes. The substrate was removed from the coat solution, immersed in a fresh coat solution with the same composition, and heated using a constant-temperature oven at 30° C. for 30 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 31

The substrate in Production Example 1 was used as a substrate. The substrate was pretreated by immersing it in 0.4 mol/L aqueous NaOH solution (pH12.0) and heating it using a constant-temperature oven at 90° C. for 15 minutes. The pretreated substrate was immersed in a solution (coat solution) containing 0.2% by mass of an acrylic acid/N,N-dimethyl acrylamide copolymer (molar ratio in copolymerization: 1/9, Mw: 800,000, manufactured by Osaka Organic Chemical Industry Ltd.) in phosphate buffer with the pH adjusted to 3.2 with citric acid, and left to stand at room temperature for 15 minutes. The substrate was removed from the coat solution, immersed in a fresh coat solution with the same composition, and heated using a constant-temperature oven at 50° C. for 30 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 4

A commercially available silicone hydrogel lens containing silicone as a main component "1day Acuvue Oasys (registered trademark)" (senofilcon A, manufactured by Johnson & Johnson) was used as a substrate. The substrate was immersed in 0.4 mol/L aqueous NaOH solution (pH12.0) and heated using a constant-temperature oven at 90° C. for 15 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 5

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 mol/L aqueous NaOH solution (pH12.0) and heating it using a constant-temperature oven at 50° C. for 10 minutes. The pretreated substrate was immersed in a solution (coat solution) containing 0.2% by mass of an acrylic acid/N-vinylpyrrolidone copolymer (molar ratio in copolymerization: 1/9, Mw: 500,000, manufactured by Osaka Organic Chemical Industry Ltd.) in phosphate buffer with the pH adjusted to 4.0 with citric acid, and left to stand at room temperature for 15 minutes. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 6

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.4 mol/L aqueous NaOH solution (pH12.0) and heating it using a constant-temperature oven at 90° C. for 15 minutes. The pretreated substrate was immersed in a solution (coat solution) containing 0.1% by mass of poly(dimethyl acrylamide) (Mw: 360,000, manufactured by Osaka Organic Chemical Industry Ltd.) in phosphate buffer with the pH adjusted to 4.0 with citric acid, and left to stand at room temperature for 15 minutes. The substrate was removed from the coat solution, immersed in a fresh coat solution with the same composition, and heated using a constant-temperature oven at 90° C. for 30 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 7

The substrate in Production Example 1 was used as a substrate. The substrate was immersed in 0.4 mol/L aqueous NaOH solution (pH12.0), and left to stand at room temperature of 23° C. for 15 minutes. Thereafter, the substrate was immersed in a solution (coat solution) containing 0.1% by mass of an acrylic acid/2-hydroxyethyl methacrylate copolymer (molar ratio in copolymerization: 1/2, Mw: 400,000, manufactured by Osaka Organic Chemical Industry Ltd.) in phosphate buffer with the pH adjusted to 3.0 with citric acid, and left to stand at room temperature for 15 minutes. The substrate was removed from the coat solution, immersed in a fresh coat solution with the same composition, and heated using a constant-temperature oven at 60° C. for 30 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 8

The substrate in Production Example 1 was used as a substrate. The substrate was pretreated by immersing it in 0.4 mol/L aqueous NaOH solution (pH12.0) and heating it using a constant-temperature oven at 90° C. for 15 minutes. The pretreated substrate was immersed in a solution (coat solution) containing 0.2% by mass of polyacrylic acid "Sokalan (registered trademark) PA110S" (Mw: 250,000, manufactured by BASF SE) in phosphate buffer with the pH adjusted to 5.0 with citric acid, and left to stand at room temperature for 15 minutes. The substrate was removed from the coat solution, immersed in a fresh coat solution with the same composition, and heated using a constant-temperature oven at 50° C. for 30 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 91

The substrate in Production Example 1 was used as a substrate. The substrate was immersed in 0.4 mol/L aqueous NaOH solution (pH12.0) and heated using a constant-temperature oven at 90° C. for 15 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 10

The substrate in Production Example 1 was used as a substrate. The substrate was immersed in 0.4 mol/L aqueous NaOH solution (pH12.0), and left to stand at room temperature (20° C. to 23° C.) for 15 minutes. Thereafter, the substrate was immersed in a solution (coat solution) containing 0.6% by mass of an acrylic acid/2-hydroxyethyl methacrylate/N,N-dimethyl acrylamide copolymer (molar ratio in copolymerization: 1/1/2, Mw: 430,000, manufactured by Osaka Organic Chemical Industry Ltd.) in phosphate buffer with the pH adjusted to 3.4 with citric acid, and left to stand at room temperature for 15 minutes. The substrate was removed from the coat solution, immersed in a fresh coat solution with the same composition, and heated using a constant-temperature oven at 40° C. for 30 minutes. The obtained medical device was washed with phosphate buffer, immersed in fresh phosphate buffer, and sterilized using an autoclave at 121° C. for 30 minutes. The results obtained by evaluation of the obtained medical device (a hydrophilic polymer layer was not observed) using the above method are shown in Tables 4 to 6.

Comparative Example 1

The substrate in Production Example 1 was used as a substrate. The substrate was pretreated by immersing it in 0.6 mol/L aqueous NaOH solution (pH12.1) and heating it using a constant-temperature oven at 40° C. for 60 minutes. The pretreated substrate was placed in a solution (coat solution) containing 0.2% by mass of an acrylic acid/2-hydroxyethyl methacrylate/N,N-dimethyl acrylamide copolymer (molar ratio in copolymerization: 1/1/8, Mw: 480,000, manufactured by Osaka Organic Chemical Industry Ltd.) in phosphate buffer with the pH adjusted to 3.6 with citric acid, and heated using an autoclave at 70° C. for 30 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Comparative Example 12

A commercially available silicone hydrogel lens containing silicone as a main component "1day Acuvue Oasys (registered trademark)" (senofilcon A, manufactured by Johnson & Johnson) was used as a substrate. The substrate was pretreated by immersing it in 0.6 mol/L aqueous NaOH solution (pH12.1) and heating it using a constant-temperature oven at 45° C. for 60 minutes. The pretreated substrate was placed in a solution (coat solution) containing 0.2% by mass of an acrylic acid/2-hydroxyethyl methacrylate/N,N-dimethyl acrylamide copolymer (molar ratio in copolymerization: 1/1/2, Mw: 550,000, manufactured by Osaka Organic Chemical Industry Ltd.) in phosphate buffer with the pH adjusted to 3.8 with citric acid, and heated using an autoclave at 70° C. for 10 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

Comparative Example 13

A commercially available hydrogel lens containing 2-hydroxyethyl methacrylate as a main component "1day Acuvue (registered trademark)" (etafilcon A, manufactured by Johnson&Johnson) was used as a substrate. The substrate was pretreated by immersing it in 0.6 mol/L aqueous NaOH solution (pH12.1) and heating it using a constant-temperature oven at 45° C. for 90 minutes. The pretreated substrate was placed in a solution (coat solution) containing 0.2% by mass of an acrylic acid/2-hydroxyethyl methacrylate/N,N-dimethyl acrylamide copolymer (molar ratio in copolymerization: 1/1/2, Mw: 550,000, manufactured by Osaka Organic Chemical Industry Ltd.) in phosphate buffer with the pH adjusted to 4.0 with citric acid, and heated using an autoclave at 70° C. for 10 minutes. The obtained medical device was washed with phosphate buffer, immersed in fresh phosphate buffer, and sterilized using an autoclave at 121° C. for 30 minutes. The results obtained by evaluation of the obtained medical device using the above method are shown in Tables 1 to 3.

TABLE 4

| | Substrate | Moisture content of substrate (% by mass) | Alkali and concentration of solution thereof | Hydrophilic polymer and concentration of solution thereof | pH before heat treatment | pH after heat treatment |
|---|---|---|---|---|---|---|
| Comparative Example 1 | "1dayAcuvueOasys" (registered trademark) | 38.0 | 0.4 mol/L aqueous NaOH solution | 0.6% by mass polyacrylic acid | 3.4 | 3.5 |
| Comparative Example 2 | "1dayAcuvueOasys" (registered trademark) | 38.0 | 0.4 mol/L aqueous NaOH solution | 0.6% by mass acrylic acid/2-hydroxyethyl methacrylate/N,N-dimethyl acrylamide copolymer | 3.4 | 3.4 |
| Comparative Example 3 | Production Example 1 | <1 | 0.4 mol/L aqueous NaOH solution | 0.2% by mass acrylic acid/N,N-dimethyl acrylamide copolymer | 3.2 | 3.3 |
| Comparative Example 4 | "1dayAcuvueOasys" (registered trademark) | 38.0 | 0.4 mol/L aqueous NaOH solution | — | — | — |
| Comparative Example 5 | "1dayAcuvueOasys" (registered trademark) | 38.0 | 0.4 mol/L aqueous NaOH solution | 0.2% by mass acrylic acid/N-vinylpyrrolidone copolymer | 4.0 | 4.1 |
| Comparative Example 6 | "1dayAcuvueOasys" (registered trademark) | 38.0 | 0.4 mol/L aqueous NaOH solution | 0.1% by mass polydimethyl acrylamide | 4.0 | 4.1 |
| Comparative Example 7 | Production Example 1 | <1 | 0.4 mol/L aqueous NaOH solution | 0.1% by mass acrylic acid/2-hydroxyethyl methacrylate copolymer | 3.0 | 3.1 |
| Comparative Example 8 | Production Example 1 | <1 | 0.4 mol/L aqueous NaOH solution | 0.2% by mass polyacrylic acid | 5.0 | 5.1 |
| Comparative Example 9 | Production Example 1 | <1 | 0.4 mol/L aqueous NaOH solution | — | — | — |
| Comparative Example 10 | Production Example 1 | <1 | 0.4 mol/L aqueous NaOH solution | 0.6% by mass acrylic acid/2-hydroxyethyl methacrylate/N,N-dimethyl acrylamide copolymer | 3.4 | 3.4 |
| Comparative Example 11 | Production Example 1 | <1 | 0.6 mol/L aqueous NaOH solution | 0.2% by mass acrylic acid/2-hydroxyethyl methacrylate/N,N-dimethyl acrylamide copolymer | 3.6 | 3.9 |
| Comparative Example 12 | "1dayAcuvueOasys" (registered trademark) | 38.0 | 0.6 mol/L aqueous NaOH solution | 0.2% by mass acrylic acid/2-hydroxyethyl methacrylate/N,N-dimethyl acrylamide copolymer | 3.8 | 4.1 |

TABLE 4-continued

|  | Substrate | Moisture content of substrate (% by mass) | Alkali and concentration of solution thereof | Hydrophilic polymer and concentration of solution thereof | pH before heat treatment | pH after heat treatment |
|---|---|---|---|---|---|---|
| Comparative Example 13 | "1day Acuvue" (registered trademark) | 58.0 | 0.6 mol/L aqueous NaOH solution | 0.2% by mass acrylic acid/ 2-hydroxyethyl methacrylate/ N,N-dimethyl acrylamide copolymer | 4.0 | 4.3 |

TABLE 5

|  | Liquid film retention time after sterilization (sec) | Frictional coefficient | Amount of mucin deposition (µg/cm$^2$) | Moisture content of medical device (% by mass) | Thickness of hydrophilic polymer layer (nm) | Percent change in moisture content (percentage point) |
|---|---|---|---|---|---|---|
| Comparative Example 1 | D (1 sec) | 0.402 | 4.8 | 38.0 | 0 | 0 |
| Comparative Example 2 | D (1 sec) | 0.302 | 3.1 | 38.0 | 0 | 0 |
| Comparative Example 3 | D (1 sec) | 0.523 | 7.8 | <1 | 0 | 0 |
| Comparative Example 4 | D (1 sec) | 0.402 | 6.5 | 38.0 | 0 | 0 |
| Comparative Example 5 | D (1 sec) | 0.411 | 5.8 | 38.0 | 0 | 0 |
| Comparative Example 6 | D (1 sec) | 0.319 | 4.5 | 38.0 | 0 | 0 |
| Comparative Example 7 | E (less than 1 sec) | 0.550 | 8.0 | <1 | 0 | 0 |
| Comparative Example 8 | E (less than 1 sec) | 0.501 | 6.1 | <1 | 0 | 0 |
| Comparative Example 9 | E (less than 1 sec) | 0.448 | 5.3 | <1 | 0 | 0 |
| Comparative Example 10 | E (less than 1 sec) | 0.421 | 6.7 | <1 | 0 | 0 |
| Comparative Example 11 | E (less than 1 sec) | 0.535 | 8.0 | <1 | 0 | 0 |
| Comparative Example 12 | D (1 sec) | 0.330 | 3.1 | 38.0 | 0 | 0 |
| Comparative Example 13 | D (1 sec) | 0.400 | 5.1 | 58.0 | 0 | 0 |

TABLE 6

|  | Amount of lipid deposition | Tensile elastic modulus of substrate (MPa) | Tensile elastic modulus of medical device (MPa) | Percent change in tensile elastic modulus (%) | Size of substrate (mm) | Size of medical device (mm) | Percent change in size (%) |
|---|---|---|---|---|---|---|---|
| Comparative Example 1 | Deposited on 1/5 of entire area | 0.70 | 0.70 | 0.2 | 14.20 | 14.20 | 0 |
| Comparative Example 2 | Deposited on 1/5 of entire area | 0.70 | 0.71 | 1.4 | 14.20 | 14.21 | 0.07 |
| Comparative Example 3 | Deposited on entire area | 0.53 | 0.53 | 0 | 14.20 | 14.20 | 0 |
| Comparative Example 4 | Deposited on 1/5 of entire area | 0.70 | 0.70 | 0.2 | 14.20 | 14.19 | −0.07 |
| Comparative Example 5 | Deposited on 1/5 of entire area | 0.70 | 0.70 | 0.1 | 14.20 | 14.19 | −0.07 |

TABLE 6-continued

| | Amount of lipid deposition | Tensile elastic modulus of substrate (MPa) | Tensile elastic modulus of medical device (MPa) | Percent change in tensile elastic modulus (%) | Size of substrate (mm) | Size of medical device (mm) | Percent change in size (%) |
|---|---|---|---|---|---|---|---|
| Comparative Example 6 | Deposited on 1/5 of entire area | 0.70 | 0.70 | 0.1 | 14.20 | 14.20 | 0 |
| Comparative Example 7 | Deposited on entire area | 0.53 | 0.53 | 0 | 14.20 | 14.20 | 0 |
| Comparative Example 8 | Deposited on entire area | 0.53 | 0.54 | 1.9 | 14.20 | 14.21 | 0.07 |
| Comparative Example 9 | Deposited on entire area | 0.53 | 0.51 | −3.8 | 14.20 | 14.21 | 0.07 |
| Comparative Example 10 | Deposited on entire area | 0.53 | 0.53 | 0 | 14.20 | 14.20 | 0 |
| Comparative Example 11 | Deposited on entire area | 0.53 | 0.53 | 0 | 14.20 | 14.21 | 0.07 |
| Comparative Example 12 | Deposited on 1/5 of entire area | 0.70 | 0.71 | 1.4 | 14.20 | 14.22 | 0.14 |
| Comparative Example 13 | No deposition | 0.30 | 0.30 | 0 | 14.20 | 14.21 | 0.07 |

The invention claimed is:

1. A method of producing a medical device comprising a substrate and a hydrophilic polymer layer, comprising the steps of:
   placing the substrate in an alkali solution and heating the substrate at a temperature ranging from 50° C. to 100° C. to obtain a pretreated substrate; and
   placing the pretreated substrate in a solution containing a hydrophilic polymer having an acidic group and a hydroxyalkyl group, and an organic acid, and heating the pretreated substrate at a temperature ranging from 50° C. to 100° C.

2. The method of producing a medical device according to claim 1, wherein the liquid film retention time of the obtained medical device is 10 seconds or longer.

3. The method of producing a medical device according to claim 1, wherein the initial pH in the step of placing the pretreated substrate in a solution containing a hydrophilic polymer and an organic acid and heating the pretreated substrate at a temperature ranging from 50° C. to 100° C. is within a range from pH2.0 to 6.0.

4. The method of producing a medical device according to claim 1, wherein the heating temperature in the step of placing the pretreated substrate in a solution containing a hydrophilic polymer and an organic acid and heating the pretreated substrate is within a range from 60° C. to 95° C.

5. The method of producing a medical device according to claim 1, wherein the hydrophilic polymer further has an amide group.

6. The method of producing a medical device according to claim 1, wherein the organic acid is one or more selected from the group consisting of acetic acid, citric acid, formic acid, ascorbic acid, trifluoromethanesulfonic acid, and methanesulfonic acid.

7. The method of producing a medical device according to claim 1, wherein the substrate comprises one or more selected from the group consisting of hydrogels, silicone hydrogels, low water content soft materials, and low water content hard materials.

8. The method of producing a medical device according to claim 7, wherein the hydrogels are one or more selected from the group consisting of tefilcon, tetrafilcon, helfilcon, mafilcon, polymacon, hioxifilcon, alfafilcon, omafilcon, hioxifilcon, nelfilcon, nesofilcon, hilafilcon, acofilcon, deltafilcon, etafilcon, focofilcon, ocufilcon, phemfilcon, methafilcon, and vilfilcon.

9. The method of producing a medical device according to claim 7, wherein the silicone hydrogels are one or more selected from the group consisting of lotrafilcon, galyfilcon, narafilcon, senofilcon, comfilcon, enfilcon, balafilcon, efrofilcon, fanfilcon, somofilcon, samfilcon, olifilcon, asmofilcon, formofilcon, stenfilcon, abafilcon, mangofilcon, riofilcon, sifilcon, larafilcon, and delefilcon.

10. The method of producing a medical device according to claim 7, wherein the low water content soft materials are materials having a silicon atom.

11. The method of producing a medical device according to claim 1, wherein the medical device is an ophthalmic lens, a skin dressing material, a wound dressing material, a skin protection material, a skin medicine carrier, an infusion tube, a gas delivery tube, a drainage tube, a blood circuit, a coating tube, a catheter, a stent, a sheath, a biosensor chip, a heart-lung machine, or an endoscope covering material.

12. The method of producing a medical device according to claim 11, wherein the ophthalmic lens is a contact lens.

* * * * *